United States Patent [19]

Loor et al.

[11] Patent Number: 5,244,785
[45] Date of Patent: Sep. 14, 1993

[54] DETERMINATION OF HIGH MOLECULAR WEIGHT ANALYTES USING A β-GALACTOSIDASE COMPLEMENTATION ASSAY

[75] Inventors: Rueyming Loor, Danville; Jeff Shindelman, Concord; Pyare L. Khanna, Fremont, all of Calif.

[73] Assignee: Microgenics Corporation, Concord, Calif.

[21] Appl. No.: 649,483

[22] Filed: Feb. 1, 1991

[51] Int. Cl.$^5$ ................ G01N 33/542; G01N 33/566; G01N 33/569
[52] U.S. Cl. ......................................... 435/5; 435/6; 435/7.6; 435/7.8; 435/18; 435/975; 436/501; 436/537
[58] Field of Search ..................... 435/7.6, 7.8, 975, 5, 435/6, 7.1, 188, 69.8, 964, 7.9, 7.93, 207, 18; 436/536, 537, 544, 547, 501

[56] References Cited

U.S. PATENT DOCUMENTS

| | | | |
|---|---|---|---|
| 4,592,998 | 6/1986 | Aurameas et al. | 435/28 |
| 4,708,929 | 11/1987 | Henderson | 435/7 |
| 4,994,385 | 2/1991 | Bieniarz et al. | 435/177 |
| 5,037,735 | 8/1991 | Khanna et al. | 435/7.6 |

FOREIGN PATENT DOCUMENTS

| | | |
|---|---|---|
| 86/02666 | 10/1985 | World Int. Prop. O. |
| 89/02597 | 9/1988 | World Int. Prop. O. |
| 90/13569 | 5/1990 | World Int. Prop. O. |

OTHER PUBLICATIONS

Yolken, R. H. "Enzyme Immunoassays for the Detection of the Infectious Antigens in Body Fluids: Current Limitations and Future Prospects", Review of Infectious Diseases, vol. 4, No. 1, (1982) pp. 35-68.

Nakamura, R. M., Voller, A., and Bidwell, D. E. "Enzyme immunoasaays: heterogenous and homogeneous systems." Handbook of Experimental Immunology in four volumes, vol. 1: Immunochemistry, D. M. Weir, Ed. (Blackwell Scientific Publications, Oxford, 1987) pp. 27.1-27.20 (4th Ed.)

Gibbons, I. et al. "Homogeneous Enzyme Immunoassay for Proteins employing β-Galactosidase," Analytical Biochemistry, vol. 102, (1980) pp. 167-170.

Wei, R. and Riebe, S. "Preparation of a Phospholipage C-Antihuman IgG Conjugate and Inhibition of its enzymatic activity by human IgG," Clinical Chemistry, vol. 23/8, (1977) pp. 1386-1388.

Hemmilä, I. "Fluoroimmunoassays and Immunofluorometric Assays," Clinical Chemistry, vol. 31(3) (1985) pp. 359-370.

Shin Lin et al., "β-galactosidase: α-Complementation of a Deletion Mutant with Cyanogen Bromide Peptides" Biochem. and Biophys. Res. Comm. (1970) 40(2): 249-254.

K. E. Langley and Irvine Zabin, "β-galactosidase α-Complementation: Properties of the Complemented Enzyme and Mechanism of the Complementation Reaction" Biochemistry (1976) 15(22):4866-4875.

Primary Examiner—David Saunders
Attorney, Agent, or Firm—Cooley Godward Castro Huddleson & Tatum

[57] ABSTRACT

A method for detecting the presence of a high-molecular-weight analyte, which uses a variation on complementation assays, comprising (1) providing an enzyme donor (ED)complex comprising ED coupled to an analyte-specific binding molecule, wherein the ED complex retains measurable complementation activity such that active β-galactosidase is formed in the presence of an enzyme acceptor (EA); (2) contacting the ED complex and EA in the presence of a sample suspected of containing a high-molecular-weight analyte that reacts specifically with the analyte-specific binding molecule; and (3) relating the presence of the analyte in the sample to the formation of active β-galactosidase enzyme.

15 Claims, 4 Drawing Sheets

DETERMINATION OF HIGH MOLECULAR WEIGHT ANALYTES USING A β-GALACTOSIDASE COMPLEMENTATION ASSAY

INTRODUCTION

1. Technical Field

The present invention relates to enzyme immunoassays and, in particular, to immunoassays using β-galactosidase as the enzyme label.

2. Background

Enzymes have been used successfully as detectable labels in a number of different immunoassays. A number of such assays have been based on the ability of fragments of β-galactosidase to complement each other and form active enzyme. In particular, a β-galactosidase enzyme donor (ED), which is a fragment from one end of the enzyme molecule, combines with a β-galactosidase enzyme acceptor (EA), a fragment from the other end of the enzyme molecule, to form active β-galactosidase enzyme. Conjugating a small analyte or an analyte analogue to the ED at certain sites does not greatly affect the complementation of ED with EA or the rate of β-galacto-sidase-catalyzed activity. However, when the ED-analyte conjugate is bound by anti-analyte antibody, complementation and the enzyme-catalyzed reaction rate during the initial phase of the reaction are reduced.

This reduction in enzyme-catalyzed reaction rate has been used to quantify analytes in a situation where both the ED-analyte conjugate present in an assay medium and the analyte present in the sample compete for anti-analyte antibody prior to the addition of EA. The β-galactosidase-catalyzed reaction rate increases as the amount of analyte present in the sample increases, because analyte in the sample reduces interaction of the ED-analyte conjugate and anti-analyte antibody, allowing more of the ED-analyte conjugate to react with the EA to form active β-galactosidase enzyme.

This technology was originally developed for low molecular weight analytes. Recent developments in β-galactosidase complementation assays have included new EA and ED molecules in which the break in continuity of the β-galactosidase chain is in the omega region at the carboxyl terminus of the chain instead of in the alpha region at the amino terminus, as was originally developed, as well as application of the technology to new assay types.

A problem exists in assays for large molecular weight analytes. In such assays there is only a small relative effect on complementation rate when a binding partner binds to the large analyte or analyte analogue attached to the ED molecule. This is not a problem with small analytes, as the attachment of a large binding protein (usually an antibody specific for the analyte) to the small analyte in such an ED-analyte conjugate causes a significant decrease in complementation activity (i.e., the rate at which active β-galactosidase is formed from the inactive ED and EA fragments). However, when a large analyte is already attached to the ED fragment, attachment of an antibody molecule or other binding partner to the large molecule makes little difference in the rate of complementation.

Accordingly, there remains a need for a new method capable of measuring high molecular weight analytes using complementation of ED and EA fragments of β-galactosidase that existing methods.

3. Relevant Literature

Modified β-galactosidase enzyme donors enzyme acceptors have been prepared by chemical synthesis and recombinant DNA engineering. The modified fragments retain β-galactosidase activity upon complementation. See, for example, U.S. Pat. No. 4,708,929 and the articles cited therein. Mutant polypeptides derived from β-galactosidase are disclosed by Langley and Zabin, Bio. Chem. (1976) 15:4866, which can complement or spontaneously restore enzyme activity when added to extracts of appropriate β-galactosidase-negative mutants. See also Lin et at., Bio. Chem. Biophys. Res. Comm. (1970) 40:249.

SUMMARY OF THE INVENTION

It is an object of this invention to provide a method and reagents for the detection and quantitative analysis, using homogeneous immunoassays system, of high molecular weight analytes that has increased sensitivity and simplicity over techniques previously available.

The present invention provides such a method and reagents by utilizing β-galactosidase donor and acceptor fragments in a new assay format. Specifically, the presence or quantity of a high-molecular-weight analyte in a sample is determined by employing complementary fragments of β-galactosidase, which fragments are defined as enzyme donor (ED) and enzyme acceptor (EA) and when bound, i.e., brought together, form active β-galactosidase, wherein the ED fragment is present in the form of an ED/specific-binding-molecule conjugate where the binding molecule, typically an antibody (Ab), is specific for the analyte. It has been found that sufficient complementation activity remains for an ED-Ab conjugate (this abbreviation being used as shorthand to designate all possible complexes of the invention that contain different types of binding molecules). This ED-Ab complementation activity is significantly affected when bound by the large analyte to be measured. In general, the complementation activity of the Ab-ED conjugate decreases in proportion to the amount of ED-Ab conjugate bound by the analyte. Thus, it is possible to determine the presence and amount of a high-molecular-weight analyte. This is in contrast to prior assays which relied on competitive antibody binding to a small analyte-ED conjugate to reduce complementation activity.

The resulting enzyme activity can be detected or measured in a variety of well-known manners, such as by using an enzyme substrate which provides a measurable product upon reaction with β-galactosidase. The amount of analyte present in a sample can thereby be determined by comparing the amount of measurable product to that formed when using a series of samples containing known amounts of analyte.

BRIEF DESCRIPTION OF THE DRAWINGS

The present invention will be better understood by reference to the following detailed description of the invention when considered in combination with the accompanying drawings, wherein.

DESCRIPTION OF SPECIFIC EMBODIMENTS

Figure 1:
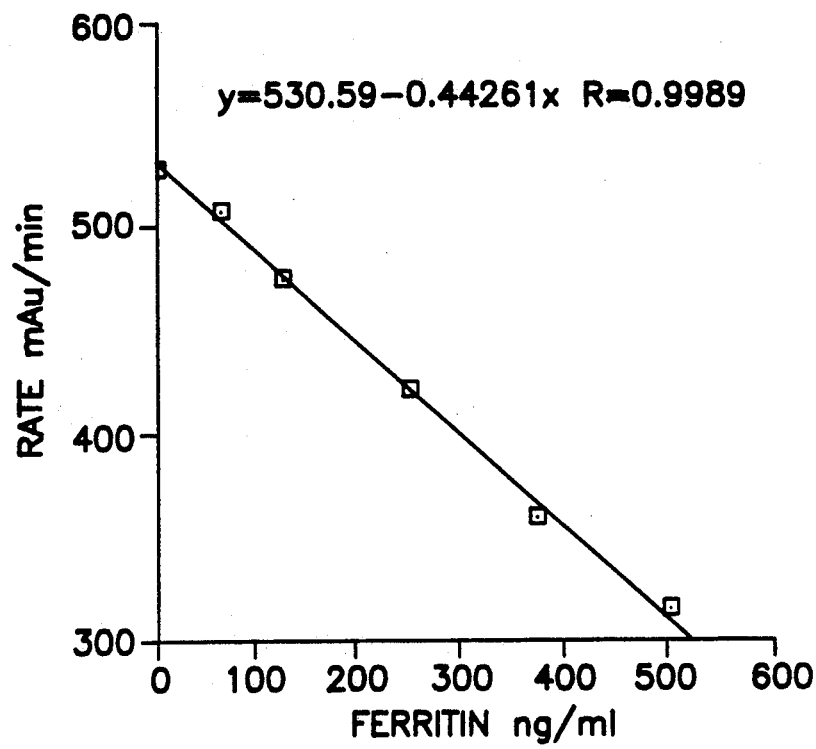
FIG. 1 is a graph showing enzyme activity following complementation in the presence of a high-molecular-weight analyte (ferritin) by assay procedure 1 of Example 1 as described herein.

The present invention comprises methods and reagents for detecting and quantitating the amount of a high-molecular-weight analyte in a sample. The method is a variation on standard complementation assays involving $\beta$-galactosidase in which inactive fragments of $\beta$-galactosidase combine in solution to form active $\beta$-galactosidase. The fragments are referred to herein as enzyme-acceptor (EA) fragments, to designate the smaller and larger fragments, respectively, of the $\beta$-galactosidase molecule.

In particular, the present invention provides a method for detecting the presence of an analyte having a high molecular weight (preferably with multivalent antigenic determinants) such that complementation activity is different in the presence and absence of binding between (1) antibody (Ab) or another binding moiety attached to an enzyme donor fragment of $\beta$-galactosidase and (2) the analyte. The rate of enzyme complementation is further reduced in the case of multivalent analytes by the addition of excess unlabelled binding moiety, which effectively increases the size of the parent analyte by binding to unoccupied binding sites. In general, the method comprises the following steps:

(a) providing an ED complex comprising ED coupled to an analyte-specific binding molecule, wherein said ED complex retains measurable complementation activity such that active $\beta$-galactosidase is formed in the presence of EA;

(b) contacting the ED complex and EA (and an excess unlabelled binding moiety in preferred embodiments using multivalent analytes) in the presence of a sample suspected of containing a high-molecular-weight analyte that reacts specifically with the analyte-specific binding molecule, and (c) relating the presence of the analyte in the sample to the formation of active $\beta$-galactosidase enzyme.

The present invention is predicated, at least in part, on the principle that the ED/binding-moiety complex and EA form active enzyme at a different rate than does the combination of EA with the ternary complex of ED/binding-moiety/high-molecular-weight analyte. When a small amount of the analyte is present, only a part of ED-Ab conjugate can bind to the analyte and hence more of ED-Ab conjugate is available for complementation with EA. To the contrary, when large amounts of analyte are present, less ED-Ab conjugate is available for complementation with EA, and hence, less enzyme activity is observed. In both cases, multivalent antigenic determinants allow the simultaneous complexation of ED-binding moiety conjugate and unlabelled anti-analyte antibody binding at multiple sites. Unlabelled antibody occupies the unbound sites and makes enzyme complementation inhibition more effective. The size of the ternary complex, consisting of ED-Ab conjugate, analyte, and unlabelled antibody becomes very large per ED molecule, and hence less complementation is observed. The quantity of the analyte, therefore, is inversely proportional to enzyme activity, which can be measured in any suitable manner, as through the use of an enzyme substrate.

The present inventive method therefore further contemplates the ED-Ab complex, EA, unlabelled antibody, and sample being contacted with an enzyme substrate which provides for a measurable product upon reaction with complemented $\beta$-galactosidase such that the amount of analyte in the sample can be determined by comparing the amount of measurable product to that formed in the presence of a known amount of analyte. The present invention also contemplates kits for use in carrying out the method of the present invention as well as individual reagents used in the method of the invention.

The ability of the ED-Ab complex of the present invention to complement with EA in the absence of analyte differs markedly from the $\beta$-galactosidase complementation phenomenon observed in a number of previously described assays employing ED and EA conjugates. For example, in the assays described in U.S. Pat. No. 4,708,929, ED conjugated to a small analyte complements with EA in the absence of anti-analyte antibodies. When the anti-analyte antibodies are present in the assay mixture, complementation activity drops significantly when compared to initial activity in the absence of antibodies. In the presence of analyte present in the unknown sample, a competition occurs between the ED-labelled analyte and the analyte present in the sample, for a limited amount of binding sites. Thus, presence of more analyte ties up more antibody and hence, allows correspondingly more ED-analyte to complement with EA. Thus, complemented enzyme activity is directly proportional to the amount of analyte in the sample. This competitive assay method works well only with small molecules.

In contrast, the present invention is a non-competitive immunoassays. An ED-binding moiety conjugate is employed as compared to ED-hapten conjugate in the previously described method. Further, the present method allows a direct assay where the analyte to be measured is used to inhibit the rate of enzyme complementation. In addition, the present assay principle works well with high molecular weight analytes preferably having multivalent antigenic determinants.

The difference in the prior teaching and the present results is believed to result from the large size of the analyte/ED-Ab/unlabelled Ab complex relative to the binding moieties. By using the present assay only when the analytes are very large, it is still possible to maintain a difference in complementation rates. Such differences would have been undetectable on the scale of complementation rates known previously for prior assays in which small analytes were attached to ED molecules and allowed to react with antibodies to reduce the complementation rate.

The ED and EA components of the present invention are partial sequences of β-galactosidase. For the purposes of the subject invention, the shorter portion of the β-galactosidase molecule is referred to as the enzyme donor (ED), and the longer portion is the enzyme acceptor (EA). The enzyme acceptor and enzyme donor are characterized by forming an active enzyme complex when brought together. The preparation of β-galactosidase enzyme donors and acceptors is described in U.S. Pat. No. 4,708,929, which disclosure is incorporated herein by reference.

Any of the previously described methods for attaching proteins to other molecules can be used to attach the ED component to the binding moiety. Especially preferred is the use of bifunctional organic linking groups to attach proteinaceous binding moieties to the ED fragment, which itself is proteinaceous. Examples of such linking groups, which are well known in protein chemistry, include dialdehydes, such as glutaraldehyde, and diamines, such as 1,6-diaminohexane as described in the specific literature (e.g., *J. Immunoassays*, 1983, 4:209).

The binding moieties are components capable of binding to the particular analyte of interest. The binding between the binding moieties and the analyte is preferably non-covalent. Suitable binding moieties preferably have higher affinity and specificity for the analyte than for the other components in a sample being analyzed. Suitable binding moieties can be of a variety of molecular categories including antibodies specific for a portion of the analyte (preferably, monoclonal antibodies); binding proteins that naturally bind to the analyte, e.g., lectins for analytes comprising a carbohydrate portion; and ligand receptors when the analyte comprises a complementary ligand, e.g., cell-surface receptors specific for proteinaceous hormones.

When the analyte is a nucleic acid, the binding moiety can be SSDNA, RNA, or any other natural or synthesized single-stranded nucleic acid. Alternatively the binding moiety could be a non-nucleic acid molecule which recognizes a specific nucleotide sequence, such as an antibody or specific DNA binding protein.

Methods for the production of antibodies or monoclonal antibodies to be used in the subject invention are known in the literature. See, e.g., U.S. Pat. No. 4,574,116 and the references cited therein, whose disclosures are herein incorporated by reference. Alternatively, monoclonal antibodies or binding fragments can be purchased commercially.

When the binding moiety is a nucleic acid molecule, the moiety will usually comprise at least 12 nucleotides, more usually at least 14 nucleotides, and preferably at least about 18 nucleotides. The size of the binding moiety will vary with the nature of the analyte, the amount of analyte in the sample, and the conditions employed in the detection process. The nucleic acid sequences for use in a binding moiety can be provided by isolation from a natural source, synthesis, or other means known in the art.

A specific binding interaction must occur between the analyte and the binding moiety in order for the assay to be able to distinguish analyte from other components in the sample. By specific binding interaction is meant that the assay can detect the presence of analyte in the presence of other components normally present in the sample. Typically, the binding moiety for the analyte binds to the analyte only but not to the other components of the sample.

The assay method of the invention can be used to detect any analyte that is sufficiently large or has multivalent antigenic sites to cause a measurable difference in complementation when bound to the ED-Ab complex (relative to complementation activity in the absence of analyte). Generally, the analyte will be a polypeptide, protein, virus particle, polysaccharide, nucleic acid, lipid, or combination thereof, such as a glycoprotein or lipoprotein.

The molecular weight of the analyte will usually be at least about 10,000, more usually at least about 20,000. Polypeptides of interest will generally be from about 10,000 to about $3 \times 10^6$ molecular weight, more usually from about 20,000 to $2 \times 10^6$ molecular weight. Where the analyte is a nucleic acid molecule, the molecule will generally range from about 12 nucleotides to about $2 \times 10^6$ nucleotides. The nucleic acid sample can involve DNA, which can be chromosomal or extrachromosomal; e.g., plasmids, viruses, synthetic constructs, or the like; or RNA, such as messenger RNA, transfer RNA, ribosomal RNA, viruses, or the like. The nucleic acid sequences can involve structural genes on translated regions, regulatory regions, introns, exons, and the like.

The protocol for the assay can be varied widely, depending upon the system being employed, the sensitivity of the assay, the speed with which the assay is to be carried out, the nature of the analyte, and the like. EA, the ED complex, unlabelled antibody (if a multivalent analyte is being detailed), and sample are combined together under appropriate conditions of stringency to allow for binding. The reagents can be combined concomitantly or added sequentially. Where the order is sequential, the reaction mixture of sample, ED complex, and buffer is preferably incubated for about 5 to 25 minutes, usually about 10 minutes, before the addition of EA, unlabelled antibody, and enzyme substrate.

The sample can be subjected to prior treatment or can be used without prior treatment. In the situation in which the analyte in the sample is capable of binding with the binding moieties, no prior sample preparation is generally necessary. In the situation in which the analyte in the sample is not immediately capable of binding with the binding moieties, prior sample preparation will be necessary. For example, where the analyte is double-stranded nucleic acid and the binding moieties are complementary nucleic acid strands, it will be necessary to treat the sample to denature the double-stranded molecules before mixing with the ED complex. Denaturation can be achieved most readily by subjecting the sample to high temperature, generally from about 90° C. to about 100° C. for about 3 to about 15 minutes. Other means for denaturation can be utilized such as treating the sample with alkaline solutions or concentrated solutions of formamide or through use of other procedures known in the art.

The assay medium is preferably buffered at a pH in the range of about 6 to 9 when using proteinaceous binding moieties, using a convenient buffer such as phosphate, Tris, or the like. The significant factor in selecting an appropriate buffer is that the buffer not inhibit the β-galactosidase enzyme reaction, complementation of EA and ED to form active β-galactosidase, or binding of the binding moiety to the analyte. Selection of buffer for use in diagnostic assays, such as the present assay, is conventional. Buffers used previously in complementation assays can be used in the method of the present invention.

The assay can be carried out at any suitable temperature which does not inhibit the desired reactions, generally at least at room temperature, which is typically at least about 20° C., but preferably at an elevated temperature below about 40° C. The assays are generally and preferably performed at atmospheric pressure.

The times required for the completion of the desired reactions vary depending on the particulars of the assays. In the situations, for example, in which the binding moiety is a nucleic acid, the time required for hybridization or binding depends on the concentration and sequence complexity of the nucleic acid probe, as well as on the assay temperature, solvent, and salt concentrations. Generally, hybridization is carried out at a temperature of about 20° C. to about 50° C. in about 0.15 M sodium chloride and 0.015 M sodium citrate for a period of about ½ hr. to about 18 hr. to allow formation of hybrids.

The techniques for the hybridization of DNA are disclosed in many references, including Walker and Gaastra (eds.) Techniques in Molecular Biology (1983) MacMillan Publishing Company, New York, pp 113–135 and 273–283; Maniatis et al., (eds) *Molecular Cloning* (1982) Cold Spring Harbor Laboratory, pp 309; E. Southern, *J. Mol. Biol.* (1975) 98:503; Botchan et al., *Cell* (1976) 9:269; Jeffreys et al., *Cell* (1977) 12:429. These disclosures are incorporated herein by reference.

The amount of sample that is used in conjunction with the present invention depends, among other things, upon the concentration of the analyte, the nature of the sample, and the sensitivity of the assay.

In the present invention, any suitable means can be used to detect and quantify the amount of active enzyme and relate the information to the detection and determination of the amount of analyte present in the sample. An enzyme substrate is generally and preferably used for such a purpose by providing a measurable product upon reaction with active β-galactosidase enzyme. The amount of analyte in the sample can then be determined by comparing the amount of measurable product to that formed in the presence of a known amount of analyte.

The enzyme substrate typically and preferably employed results in a change in the amount of light absorbance (optical density) or emission of the assay medium when cleaved by the active enzyme. That is, cleavage of the substrate results in the appearance or disappearance of a colored or fluorescent product. Preferred enzyme substrates include o-nitrophenyl galactoside (ONPG) and chlorophenol red-β-galactoside (CPRG). ONPG, CPRG, and other comparable enzyme substrates are commercially available. ONPG is generally used in a concentration of from about 0.5 to about 2.0 mg/ml. Other substrates are used in concentrations to provide comparable signals to ONPG.

Where the ED-Ab complex and EA are combined in an appropriate assay medium with the enzyme substrate followed by the subsequent addition of the sample, a first reading can be taken to provide a background measurement of enzyme activity. The essential requirement of this background activity is that it be distinguishable from activity in the presence of the detectable limit of analyte.

After addition of the sample, one or more additional readings can be taken after incubation, the interval varying from about 1 minute to about 1 hour, usually about 5 minutes to about 15 minutes, between the readings. While a single reading can be taken, it is usually desirable to take more than one reading so that common errors can be cancelled out. Preferably, standard solutions are prepared of known concentrations of analyte to serve as standards for comparison with the sample. In this way, accurate quantitative determinations can be obtained.

The present invention also contemplates a kit containing reagents for carrying out the present inventive method. The kit comprises in at least one container, usually in separate containers, a β-galactosidase enzyme donor complex of the invention, an enzyme acceptor, and (in preferred embodiments) unlabelled anti-analyte antibody. The container(s) of enzyme donor complex and enzyme acceptor can additionally contain enzyme substrate, or enzyme substrate can be provided separately. Alternatively, the kits can be configured so that they contain ED attached to a linking group or a precursor of a linking group, without a binding moiety. Upon attachment of particular binding moieties to the ED linking elements of the kit, the desired analyte of interest can be assayed. In such cases the linking elements can be terminated by reactive functional groups for ease of attaching to binding moieties supplied by the end user.

The following two examples are offered by way of illustration and not by way of limitation of the present invention.

EXAMPLE 1

Assay Principle

In this assay the ferritin molecule, having a molecular weight of 480,000, inhibited the ability of an enzyme donor (ED) molecule to which an antibody specific for ferritin was bound to complement with an enzyme acceptor (EA) molecule to form active β-galactosidase. The amount of inhibition was proportional to the concentration of ferritin. In other words, the higher the concentration of ferritin, the lower the activity of β-galactosidase in the assay medium, as measured by color formation resulting from reaction of substrate with β-galactosidase.

In the homogeneous assay for the measurement of ferritin, samples containing ferritin were incubated for 5–10 minutes at 37° C. with an ED-Ab conjugate. The ED-Ab conjugate was a covalently linked complex between an ED and an antibody using a cross-linking agent. After incubation, a first reagent (designated R1) containing an antibody complex of antibody to ferritin and secondary antibody was added and incubated for 5–10 minutes. The R1 reagent also contained the substrate for β-galactosidase. The second reagent (designated R2) containing EA was then added to the assay mixture, and the color signal of the hydrolyzed substrate was spectrophotometrically measured after 4–10 minutes. The ferritin amounts in samples were determined using a calibration curve that was constructed from assay results of a series of samples containing known concentrations of ferritin.

Materials

Goat anti-ferritin antibody purified by affinity column chromatography was purchased from BiosPacific, Inc. The hetero-bifunctional crosslinking reagent, sulfo-SMCC, was obtained from Pierce Chemical Company. Chlorophenol red β-galactoside (CPRG) was purchased from Boehringer Mannheim. Enzyme Donor and Enzyme Acceptor (as used in commercial complementation assays) were obtained from Microgenics, Inc. Other chemicals were purchased from Sigma Chemical Co.

Conjugate Preparation

The goat anti-ferritin antibody, 1 mg in 0.5 ml Buffer A (50 mM sodium phosphate, pH 7.4, containing 0.15 M NaCl), was incubated with 50 ||1 of 20 mM sulfo-SMCC in Buffer A for 15 minutes at room temperature. After the incubation, the mixture was loaded on a gel filtration column (PD10, Pharmacia-LKB) and eluted with Buffer A. The fractions were monitored by absorbance at 280 nm, and void fractions containing antibody were pooled. One mg ED (ED4) in 0.5 ml Buffer A was then added to the pooled fractions and incubated for 1 hour at room temperature. The mixture containing conjugate was concentrated to 200 µl using an Amicon concentrator. The concentrate was loaded on a FPLC SUPEROSE 12 gel filtration column and eluted with Buffer B [50 mM sodium phosphate, pH 7.4, 500 mM NaCl, 0.05% Tween 20, and 0.05 mM DTT (dithiothyreitol)]. The fractions were monitored by absorbance at 280 nm and by complementation activity. The fractions containing antibody and complementation activity wer pooled and used as the conjugate.

Assay Procedures

Procedure 1. The assay was performed on a COBAS BIO centrifugal analyzer. An aliquot of 75 µl of sample or calibrator was incubated with 75 µl of conjugate in the Cobas Bio sample cups in Buffer C for 10 minutes at 37° C. Buffer C contains 0.1 M MOPS, pH 7.0, 0.4 M NaCl, 50 mM EGTA, 3 mM magnesium acetate, 0.05% Tween 20, 0.05 mM DTT, 3% ethylene glycol, and 20 mM sodium azide. After incubation, the sample cup was placed on the Cobas Bio and 25 µl of the mixture was pipetted and incubated with 155 µl of R1 reagent containing anti-ferritin antibody, secondary antibody, and substrate (CPRG) in Buffer C, followed by incubation at 37° C. for 5 minutes. Thirty µl of reagent R2 containing EA in Buffer C was then added and incubated for an additional 5–10 minutes at 37° C. The reaction rate was determined by measuring absorbance at 570 nm for each sample and standard solution.

Procedure 2. The assay procedure 2 was performed on a Cobas MIRA analyzer. The analyzer pipetted 30 µl sample or calibrator from the sample cup and 100 µl R1 reagent into cuvettes and incubated for 14 minutes at 37° C. The R1 reagent contained the Ab-ED conjugate and the substrate (CPRG) in buffer C. incubated for 3–7 minutes at 37° C. The R2 reagent contained EA, anti-ferritin antibody, and secondary antibody in the buffer C. The reaction rate was determined by measuring absorbance at 550 nm for each sample and standard solution.

Results

Figure 2:
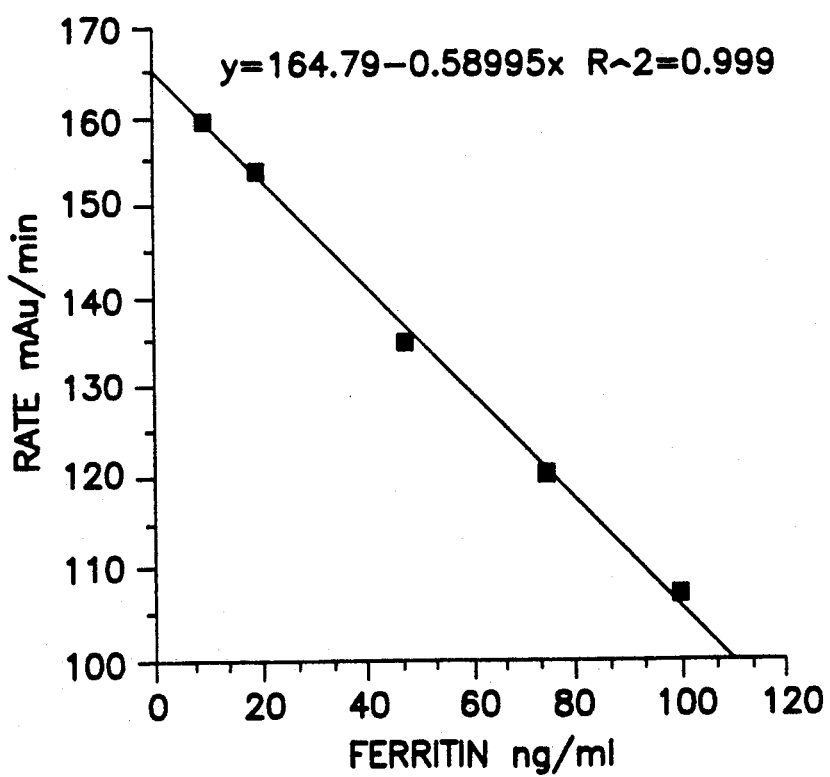
FIG. 2 is a graph showing enzyme activity following complementation in the presence of low concentrations of a high-molecular-weight analyte (ferritin), thereby showing assay sensitivity by assay procedure 1.
Figure 3:
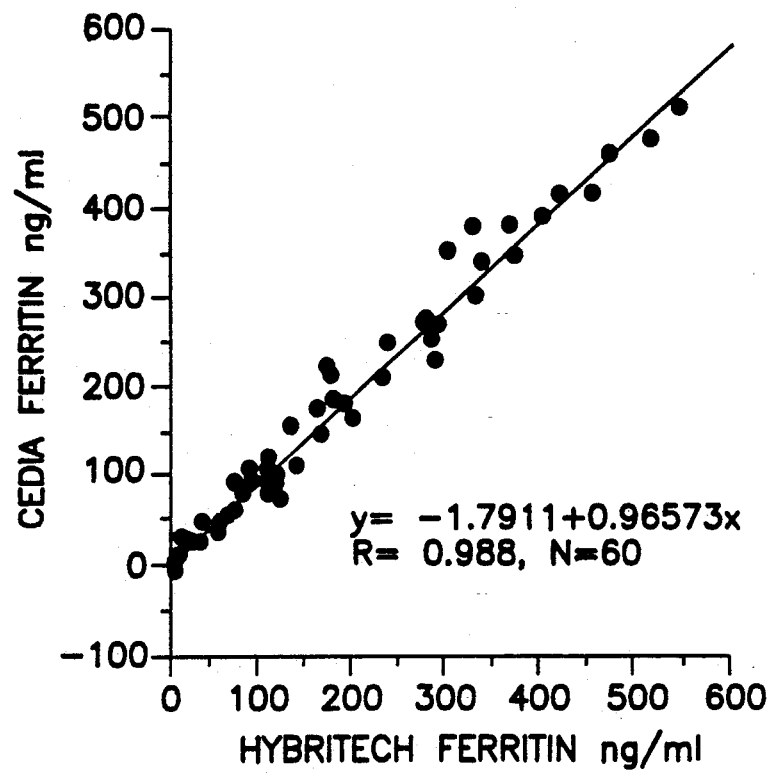
FIG. 3 is a graph showing correlation between an assay of the invention and an FDA-approved assay for ferritin by assay procedure 1.
Figure 5:
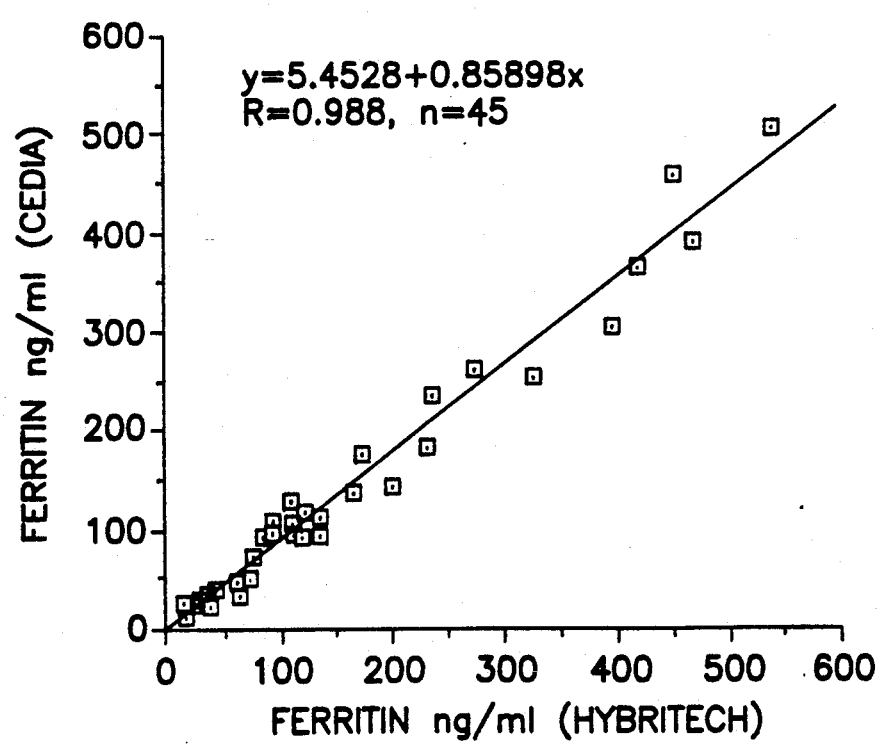
FIG. 5 is a graph showing correlation between an assay of the invention and an FDA-approved assay for ferritin by assay procedure 2.
Figure 4:
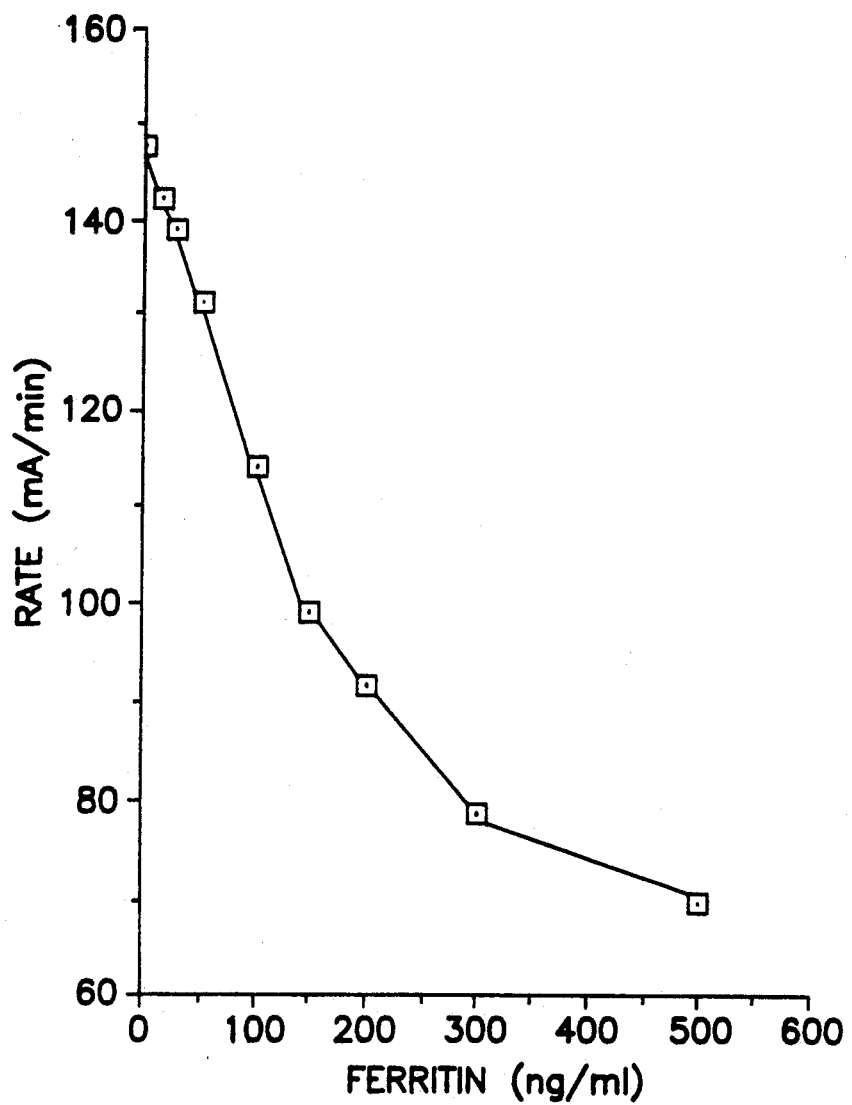
FIG. 4 is a graph showing enzyme activity following complementation in the presence of a high-molecular-weight analyte (ferritin) by assay procedure 2 of Example 1 as described herein.

A calibration curve was constructed using a series of known ferritin concentrations from 0 to 500 ng/ml. The calibration curve is shown in FIG. 1 (procedure 1) or FIG. 4 (procedure 2). The calibration curve is linear from a high rate (measured in mAU/min) for zero ferritin concentration to a low rate at 500 ng/ml ferritin. A highly sensitive calibration curve for the detection of low-end concentrations of ferritin is shown in FIG. 2. Using the calibration curve of FIG. 2 or FIG. 4, a detection sensitivity of 6 ng/ml ferritin is achieved by this homogeneous assay procedure. The ferritin concentrations in 72 human sera have been correctly measured by the assay of the invention as indicated by comparison to a FDA-approved reference procedure. The correlation curve is shown in FIG. 3. As shown in FIG. 5, the procedure 2 also measured ferritin in 45 human sera correctly. This method provides a fully automated, fast and accurate homogeneous immunoassays for ferritin unlike the other methods which require multiple steps and require complex instrumentation.

EXAMPLE 2

Assay Principle

In this assay the C-Reactive Protein molecule, having a molecular weight of 125,000, inhibited the ability of an enzyme donor (ED) molecule to which an antibody specific for C-Reactive Protein was bound to complement with an enzyme acceptor (EA) molecule to form active β-galactosidase. The amount of inhibition was proportional to the concentration of C-Reactive Protein. In other words, the higher the concentration of C-Reactive Protein, the lower the activity of β-galactosidase in the assay medium, as measured by color formation resulting from reaction of substrate In the homogeneous assay for the measurement of C-Reactive Protein, samples containing C-Reactive Protein were incubated for 5–10 min at 37° with an ED-Ab(monoclonal) conjugate and another unconjugated Ab(monoclonal). The ED-Ab conjugate was a covalently linked complex between an ED and an Ab using a cross-linking agent. After incubation, a first reagent (designated RI) containing a secondary antibody to mouse IgG and a substrate for β-galactosidase was added and incubated for 5–10 minutes. The second reagent (designated R2) containing EA was then added to the assay mixture, and the color signal of the hydrolyzed substrate was spectrophotometrically masurede after 4–10 minutes. The C-reactive protein amounts in samples were determined using a calibration curve that was constructed from assay results of a series of samples containing known concentrations of C-reactive protein.

Materials

Monoclonal anti-C-reactive protein antibodies were purchased from Medix Biochemica. The hetero-bifunctional crosslinking reagent, sulfo-SMCC, was obtained from Pierce Chemical Company. Chlorophenol red β-galactoside (CPRG) was purchased from Boehring Mannheim. Enzyme Donor and Enzyme Acceptor (as used in commercial complementation assays) were obtained from Microgenics, Inc. Other chemicals were purchased from Sigma Chemical Co.

Conjugate Preparation

The monoclonal anti-C-reactive protein antibody, 1 mg in 0.5 ml Buffer A (50 mM sodium phosphate, pH 7.4, containing 0.15 M NaCl), was incubated with 50 µl of 20 mM sulfo-SMCC in Buffer A for 15 mins at room temperature. After the incubation, the mixture was loaded on a gel filtration column (PD10, Pharmacia-LKB) and eluted with Buffer A. The fractions were monitored by absorbance at 280 nm, and void fractions containing antibody were pooled. One mg ED (ED4) in 0.5 ml Buffer A was then added to the pooled fractions and incubated for 1 hour at room temperature. The mixture containing conjugate was concentrated to 200 µl using an Amicon concentrator. The concentrate was loaded on a FPLC Superose 12 gel filtration column and eluted with Buffer B [50 mM sodium phosphate, pH 7.4, 500 mM NaCl, 0.05% Tween 20, and 0.05 mM DTT (dithiothy-reitol)]. The fractions were monitored by absorbance at 280 nm and by complementation activity. The fractions containing antibody and complementation activity were pooled and used as the conjugate.

Assay Procedures

The assay was performed on a Cobas Bio centrifugal analyzer. An aliquot of sample was diluted 10-fold with EGTA buffer. An aliquot of 10.5 μl of the diluted sample was incubated with 129.5 μl of conjugated and unconjugated anti-C-reactive protein antibody in EGTA buffer for 10 min at 37°. Cobas Bio and 10 μl of the mixture was pipetted and incubated with 175 μl of R1 reagent containing secondary antibody and substrate (CPRG) in EGTA. buffer. Incubation at this step was for 10 min. Thirty μl of reagent R2 containing EA in Buffer C was 10 then added and incubated for an additional 5–10 min at 37° C. The reaction rate was determined by measuring absorbance at 574 nM for each sample and standard solution.

EGTA buffer contains 150 mM potassium phosphate, 100 mM sodium phosphate, 3 mM magnesium acetate, 0.05% Tween 20, 0.05 mM DTT, 1.2% ethylene glycol, and 20 mM sodium azide, at a final pH 7.0.

Results

Figure 6:
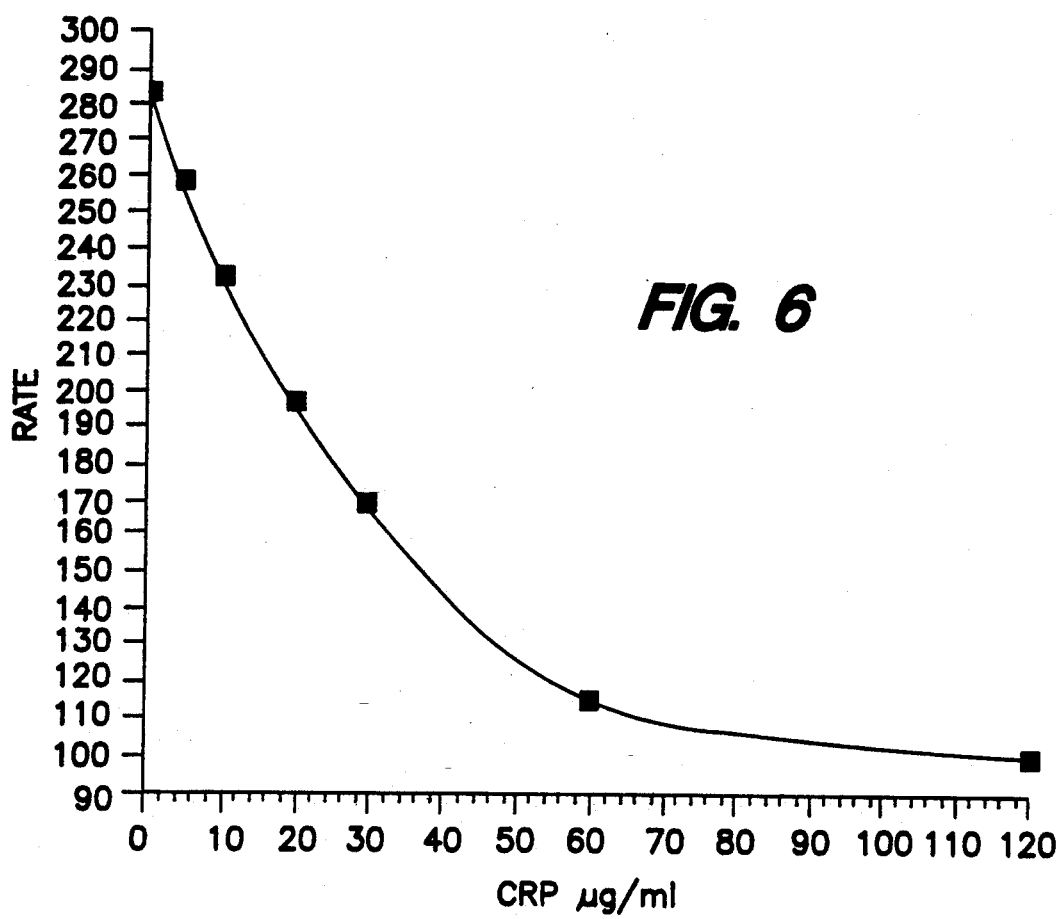
FIG. 6 is a graph showing enzyme activity following complementation in the presence of C-reactive protein as described in the procedure for Example 2 as described herein.
Figure 7:
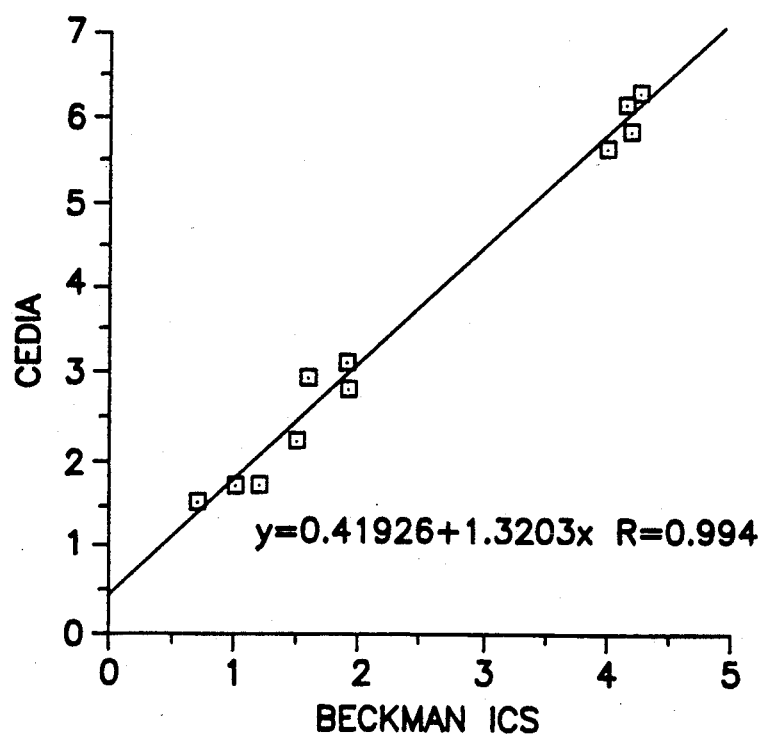
FIG. 7 is a graph showing correlation between an assay of the invention and an FDA-approved assay for C-reactive protein as described in the procedure for Example 2.

A calibration curve was constructed using a series of known C-reactive-protein concentrations from 0 to 120 μg/ml. The calibration curve is shown in FIG. 6. The calibration curve is a non-linear curve from a high rate (measured in mAu/min) for zero C-reactive protein to a low rate at 120 μg/ml C-reactive protein. The use of a non-linear curve allows for low end sensitivity while maintaining a broad assay range. Using the calibration curve of FIG. 6, a detection sensitivity of 1 μg/ml C-reactive protein can be achieved. The C-reactive protein concentrations in 11 human sera have been correctly measured by the assay of the invention as indicated by comparison to a FDA-approved reference procedure. The correlation curve is shown in FIG. 7.

It is evident from the above results that the subject method provides for an accurate, sensitive, and rapid technique for detecting levels of high-molecular-weight analytes, particularly in a complex mixture. The observed enzyme activity is inversely proportional to the amount of analyte in the sample.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims.

What is claimed is:

1. A method for detecting the presence of an analyte having a molecular weight of at least 10,000 daltons using a β-galactosidase complementation assay, comprising:
    (a) providing an enzyme donor (ED) complex comprising ED coupled to a binding moiety that reacts specifically with said analyte, wherein said D complex retains measurable complementation activity such that active β-galactosidase is formed in the present of enzyme acceptor (EA);
    (b) contacting the ED complex and EA in the presence of a sample suspected of containing said analyte, and
    (c) relating the presence of the analyte in the sample to the formation of active β-galactoside enzyme.

2. A method according to claim 1, wherein said ED complex, EA, and sample are contacted with an enzyme substrate which provides a measurable product upon reaction with β-galactosidase, the measurable product provided by the reaction of the enzyme substrate and active enzyme is measured, and the amount of said analyte in the sample is determined by comparing the amount of measurable product to that formed from a known amount of analyte.

3. A method according to claim 2, wherein said enzyme substrate is chlorophenol red β-galactoside.

4. A method according to claim 1, wherein excess unlabelled polyclonal or monoclonal antibody specific for said analyte s also present when said ED complex is contacted with EA in the present of said analyte.

5. A method according to claim 1, wherein said analyte is a polypeptide.

6. A method according to claim 1, wherein said analyte has a molecular weight of at least 20,000 daltons.

7. A method according to claim 6, wherein id binding moiety is a DNA or RNA.

8. A method according to claim 1, wherein said analyte is a nucleic acid.

9. A method according to claim 8, wherein id nucleic acid is DNA.

10. A method according to claim 8, wherein said nucleic acid is RNA.

11. A method according to claim 1, wherein said analyte is a virus particle.

12. A method according to claim 1, wherein said binding moiety is an antibody or a natural receptor.

13. A method according to claim 12, wherein said antibody is a monoclonal antibody or recombinant peptide fragment equivalent of an antibody.

14. A method according to claim 1, wherein said ED is linked to an antibody specific for said analyte by a bifunctional organic linking group.

15. A method according to claim 1, wherein said ED complex is a recombinant fusion protein.

* * * * *